United States Patent [19]

Fariello

[11] 4,255,448

[45] Mar. 10, 1981

[54] METHOD FOR REDUCING EPILEPTIFORM ACTIVITY

[75] Inventor: Ruggero G. Fariello, Madison, Wis.

[73] Assignee: Wisconsin Alumni Research Foundation, Madison, Wis.

[21] Appl. No.: 74,049

[22] Filed: Sep. 10, 1979

[51] Int. Cl.³ .......................................... A61K 31/185
[52] U.S. Cl. ..................................................... 424/315
[58] Field of Search ................................ 424/315, 319

[56] References Cited

PUBLICATIONS

Krnjevic, K, *Physiol. Rev.*, 54: 418–540, (1974).

*Primary Examiner*—Stanley J. Friedman
*Attorney, Agent, or Firm*—McDougall, Hersh & Scott

[57] ABSTRACT

Epileptiform activity can be reduced by administration of 3 amino propanesulfonic acid which penetrates the blood-brain barrier for effect as an antiepileptogenic agent.

2 Claims, No Drawings

METHOD FOR REDUCING EPILEPTIFORM ACTIVITY

This invention relates to the treatment of brain disorders by treatment with 3-aminopropanesulfonic acid (3APS).

Slightly more than 20 years ago Hayashi first described the inhibitory action of γ-aminobutyric acid (GABA) on the central nervous system (Hayashi, T. 1959. The inhibitory action of β-hydroxy γ-aminobutyric acid upon the seizure following stimulation of the motor cortex of the dog. *J. Physiol (London)* 145: 570–578 ). The initial enthusiasm for the possible use of GABA in the treatment of convulsive disorders was subsequently quenched by the observation of the relative impermeability of the blood-brain barrier of GABA.

It is now well established that naturally occurring, short-chain ω-amino acids such as glycine, β-alanine, GABA, and taurine all possess powerfull inhibitory actions at various levels within the mammalian central nervous system (Krnjevic, K. 1974. Chemical nature of synaptic transmission in vertebrates. *Physiol. Rev.* 54: 418–540). The demonstration of an anticonvulsant effect after systemic administration is an essential prerequisite for possible therapeutic application. A defect in system utilizing GABA as a neurotransmitter has been long suspected but never directly proven. Nevertheless major efforts toward a breakthrough in treatment of epilepsy are devoted to the search for an effective GABA-mimetic drug.

The following is a general outline of a series of tests that were performed by injection of inhibitory ω-amine acids including gamma aminobutyric acid (GABA), 3-aminopropane sulfonic acid (3-APS), taurine (TAU) and β-alanine (BALA).

Twenty adult cats of either sex were used. Under general anesthesia with Na-pentobarbital, acute epileptic foci were induced by injection of 5 μl of various epileptogenic agents (2% conjugated estrogens, 5% pentamethylentetrazole, 500,000 IU sodium penicillin (G) in the right postcruciate cortex or in the basocortical amygdala. Other animals were initially anesthetized with intraperitoneal Ketamine, rendered epileptic, prepared for recording, then paralyzed with Flaxedil, and artificially ventilated while effective analgesia was maintained by repetitive administration of Xylocaine in all wounds and pressure points. EEG recordings were obtained from silver ball electrodes directly applied to the pial surface near the cortical focus and by screw electrodes implanted in the skull. Recordings from amygdala were obtained from a bipolar concentric electrode stereotaxically inserted in the proximity of the focus. A catheter implanted in the femoral artery allowed continuous monitoring of arterial blood pressure on a separate polygraph. Expired $CO_2$ was also monitored and, in artifically ventilated animals, ventilation was adjusted to $CO_2$ concentrations between 3.2 and 3.9%. Amino acids were dissolved in 0.9% saline solution except for 3-APS which was dissolved in 0.1 M acetic acid. Each solution contained 100 mg amino acid/ml. Solutions were then adjusted to pH values 5.5 to 8.0. After the onset of epileptiform spikes, baseline recording was carried on for 60 to 90 min. Amino acids were then injected intravenously through a catheter previously implanted in the femoral vein. The possible anticonvulsant effect of the amino acids was assessed by the spike frequency histogram of 2-min epochs throughout the experiments. Spike amplitude and possible changes in background EEG activity were also evaluated.

Eight animals received multiple amino acid injections. However, no amino acids were administered after taurine because of the possibility of a prolonged inhibitory effect. Control injections of equal volumes of the vehicles at various pH were also tested.

Subjects with amygdaloid and cortical foci did not show different responses to administered amino acids. Injections of the control solutions of equal volume and pH did not affect epileptic spike activity. Short-lasting inhibitory effects on focal spiking were noted with 80 mg/kg β-alanine, GABA, taurine, and 3-APS. Particularly powerful was the action of 3-APS which totally suppressed spiking activity for 35 seconds and significantly reduced spike frequency for more than 8 min. after injection (average spike reduction, 38%). In animals anesthetized with pentobarbital, spikes which reappeared after the initial suppression were seen to originate from barbiturate spindles; these inhibitory effects lasted 50 to 150% longer than in nonbarbiturate-treated animals. In these subjects GABA, taurine, and 3-APS, besides influencing spiking activity, had remarkable systemic effects. These consisted of bradycardia, transitory depression of respiration, and a decrease in blood pressure. A blood pressure decrease of as much as 25% of the baseline value was noted when doses of 3-APS exceeded 50 mg/kg. Similar and even greater pressure decreases were induced by acetylcholine (20 μg) hexamethonium chloride (20 mg/kg) without affecting focal spiking. In an attempt to establish the minimal effective dose, in some experiments serially decreasing doses of amino acids were administered. The effective threshold dose was 80 mg/kg for GABA and β-alanine, 50 mg/kg for taurine, and 5 mg/kg for 3-APS. Thus 3-APS was 10 times more powerful than the next more effective inhibitory amino acid. At threshold dose taurine and 3-APS did not cause systemic effects. A transient depression of EEG background activity was occasionally noted with GABA (80 mg/kg), taurine (50 mg/kg), and 3-APS (25 mg/kg); spike amplitude was never affected.

All the tested amino acids proved capable of transiently inhibiting firing from acute neocortical and limbic epileptic foci. The absence of any effect on spiking activity after injection of control solutions of equal volume and pH ruled out any nonspecific action due to the physical or chemical properties of the vehicle rather than to the amino acids themselves. The various compounds tested displayed a spectrum of potency progressively increasing from β-alanine to GABA and taurine and was maximal with 3-APS. This spectrum closely parallels the potency of the depressant actions of these amino acids when iontophoretically tested on mammalian cortical neurons. (Crawford, J. M., and D. R. Curtis, 1964. The excitation and depression of mammalian cortical neurones by amino acids. *Br. J. Pharmacol.* 23: 313–329 ).

GABA is reported to be unable to cross the blood-brain barrier. However, after intracarotid injection physiologic effects were noted that were compatible with a direct central action of GABA. Furthermore, intravenous GABA is capable of terminating epileptiform after-discharges elicited on isolated slabs of cortex.

Taurine was effective at doses from 50 to 80 mg/kg. This amino acid easily crosses the blood-brain barrier in mammals (Urquhart, N., T. L. Perry, S. Hansen, and H. Kennedy. 1974. Passage of taurine into adult mammalian brain. *J. Neurochem.* 22: 871-872 ). The selective antiepileptic activity of taurine and lack of effect of its main metabolite, isethionic acid, have been extensively documented. In other, similar experiments, taurine was reported to have an initial as well as a delayed effect on cortical epileptic firing (Mutani, R., L. Bergamini, R. Fariello and M. Delsedime. 1976. Effects of taurine on cortical acute epileptic foci. *Brain Res.* 70: 170-173). The present invention deals with more active epileptic foci and smaller doses of taurine; no delayed effect was detected in such conditions and the initial effect was of much briefer duration.

The most powerful suppressant action, both in terms of duration and threshold, was noted after 3-APS administration. In some animals under barbiturate anesthesia 3-APS also caused systemic effects. In particular, a decreased cerebral perfusion due to arterial hypotension might have been responsible for the observed spike inhibition. Against this hypothesis two factors should be emphasized. First, the anticonvulsant effect was noted in some experiments without the concomitant decrease in blood pressure. Second, when equal or greater hypotensive states were induced by i.v. acetylcholine and hexamethonium, spiking activity remained unaffected. Still, without direct measurements of 3-APS in the brain, it is not possible to determine whether the inhibitory effect was due to the presence of 3-APS itself in the brain or to some metabolite. However, the fact that iontophoretically administered 3-APS has powerful and long-lasting suppressant action on cortical neuronal firing suggests that the spike inhibition observed may be related to a direct action of 3-APS on epileptic neurons. Furthermore, 3-APS seems to inhibit GABA transaminase activity, a factor which may have relevance to its anticonvulsant activity.

GABA, taurine, and 3-APS had longer-lasting effects in animals under barbituate anesthesia.

From the foregoing, it will be seen that systemically administered inhibitory amino acids can transiently suppress the electrical paroxysmal activity of epileptic foci without significantly affecting other EEG rhythms. Physiological investigations have demonstrated that 3-APS is a GABA agonist within as well as outside the central nervous system. Biochemical studies have shown that 3-APS competes with GABA for binding with its receptor. In fact, such receptor binding has higher affinity for 3-APS than for GABA itself.

I claim:

1. A method for reducing epileptiform activity comprising administering an effective amount to one having epileptiform activity from 3-aminopropane sulfonic acid.

2. A method as claimed in claim 1 in which the threshold dosage of 3-Aminopropane-sulfonic acid is 5 mg per Kg of recipient.

* * * * *

UNITED STATES PATENT OFFICE
CERTIFICATE OF CORRECTION

Patent No. 4,255,448          Dated March 10, 1981

Inventor(s) Ruggero G. Fariello

It is certified that error appears in the above-identified patent and that said Letters Patent are hereby corrected as shown below:

Kindly enter the following before the first paragraph on page 1:

-- The invention described herein was made in the course of work under a grant or award from the Department of Health, Education and Welfare. --

Signed and Sealed this

*Ninth* Day of *June 1981*

[SEAL]

*Attest:*

RENE D. TEGTMEYER

*Attesting Officer*     *Acting Commissioner of Patents and Trademarks*